US009694882B2

(12) United States Patent
Lee et al.

(10) Patent No.: US 9,694,882 B2
(45) Date of Patent: Jul. 4, 2017

(54) SYSTEM, APPARATUS, AND PROCEDURE FOR PROVIDING ROUTE SUGGESTIONS

(71) Applicant: Garmin Switzerland GmbH, Schaffhausen (CH)

(72) Inventors: Wai C. Lee, Overland Park, KS (US); Claudette D. Stevenson, Olathe, KS (US)

(73) Assignee: Garmin Switzerland GmbH (CH)

( * ) Notice: Subject to any disclaimer, the term of this patent is extended or adjusted under 35 U.S.C. 154(b) by 4 days.

(21) Appl. No.: 14/987,433

(22) Filed: Jan. 4, 2016

(65) Prior Publication Data

US 2016/0114869 A1 Apr. 28, 2016

Related U.S. Application Data

(63) Continuation of application No. 14/206,972, filed on Mar. 12, 2014, now Pat. No. 9,255,807.

(60) Provisional application No. 61/792,704, filed on Mar. 15, 2013.

(51) Int. Cl.
| | |
|---|---|
| *B63B 49/00* | (2006.01) |
| *G01C 21/20* | (2006.01) |
| *G01C 21/34* | (2006.01) |
| *G01S 19/19* | (2010.01) |
| *G06F 19/00* | (2011.01) |

(52) U.S. Cl.
CPC .............. *B63B 49/00* (2013.01); *G01C 21/20* (2013.01); *G01C 21/34* (2013.01); *G01C 21/3407* (2013.01); *G01C 21/3484* (2013.01); *G01S 19/19* (2013.01); *G06F 19/3481* (2013.01)

(58) Field of Classification Search
CPC .... B63B 49/00; G01C 21/34; G01C 21/3407; G01C 21/3484; G01C 21/20; G01S 19/19; G06F 19/3481
USPC ......................................................... 701/428
See application file for complete search history.

(56) References Cited

U.S. PATENT DOCUMENTS

| 8,031,595 | B2 | 10/2011 | Hamilton, II et al. ........ 370/230 |
|---|---|---|---|
| 8,332,146 | B2 | 12/2012 | Rosing et al. ................ 701/468 |
| 2008/0294337 | A1 | 11/2008 | Dawson et al. .............. 701/209 |
| 2009/0319230 | A1 | 12/2009 | Case et al. .................... 702/182 |
| 2010/0191461 | A1 | 7/2010 | Zeng ............................ 701/200 |

OTHER PUBLICATIONS

Printout from http://aboutfoursquare.com/create-your-foursquare-heat-map-with-where-do-you-go/; published prior to Mar. 12, 2014.
(Continued)

*Primary Examiner* — Brian P Sweeney
(74) *Attorney, Agent, or Firm* — Samuel M. Korte; Max M. Ali (57) ABSTRACT

An apparatus or web server for assisting a user in selecting a route based on tracked popularity of routes traveled by other users and a desired user activity. The apparatus may include a memory for receiving and storing route data for routes previously traveled by a plurality of users and a processing device coupled with the memory for receiving desired route characteristic information from the user, including a desired activity type, such as running or cycling. The processing device may compare the desired route characteristics information with the route data, suggest at least one of the stored routes to the user based on the comparison, and visually indicate with a color-coded heat map a popularity of the routes suggested based on the comparison.

20 Claims, 6 Drawing Sheets

(56) References Cited

OTHER PUBLICATIONS

Printout from http://lehrblogger.com/2010/03/19/where-do-you-go published prior to Mar. 12, 2014.
Printout from http://www.wheredoyougo.net/ published prior to Mar. 12, 2014.
Printout from http://www.thewire.com/national/2014/02/cities-mapped-where-their-people-go-running/357792/ published prior to Mar. 12, 2014.
Printout from http://flowingdata.com/2014/02/05/where-people-run published prior to Mar. 12, 2014.
Printout from http://www.runtheline.com/1552/nike-sportswatch-gps-running-watch-review# published prior to Mar. 12, 2014.
Printout from http://flowingdata.com/2013/11/11/running-traces/ published prior to Mar. 12, 2014.
Printout from https://maps.google.com/maps?hg=http://maps.google.com/help/maps/directions/biking/mapleft.kml&ie=UTF8&ll=37.687624.-122.319717&spn=0.346132.0727158&z=11&lci=bike&dirflg=b&f=d published prior to Mar. 12, 2014.

SYSTEM, APPARATUS, AND PROCEDURE FOR PROVIDING ROUTE SUGGESTIONS

RELATED APPLICATIONS

The present application is a continuation of, and claims priority benefit to, co-pending and commonly assigned U.S. non-provisional patent application entitled, "SYSTEM, APPARATUS, AND PROCEDURE FOR PROVIDING ROUTE SUGGESTIONS," application Ser. No. 14/206,972, filed Mar. 12, 2014, which claims the benefit under 35 U.S.C. §119(e) of provisional U.S. Patent Application entitled, "Heat Map of Frequently Traveled Paths," Application Ser. No. 61/792,704, filed Mar. 15, 2013. The above applications are hereby incorporated by reference into the current application in their entirety.

BACKGROUND

Runners and cyclists frequently use fitness watches and other electronic devices to track distance, time, speed, and the like, as well as to record their traveled routes for future reference. Data gathered by these devices is often reviewed by the user and shared with others.

SUMMARY

Runners and cyclists frequently desire to find new routes suitable for running, cycling, and other activities. Runners and cyclists may prefer to run or bike on routes that are frequently traveled by others or avoid such frequently-traveled routes. Users may also prefer to travel along routes that have been previously traveled by other users having equipment that is similar to the user's equipment. Though some existing software and handheld devices will identify and suggest a path to travel that is suitable for user workouts based on fitness criteria and/or geographic locations provided by the user, these existing technologies do not take the activities of other users into consideration when identifying a path for travel.

Embodiments of the present technology provide a web server or other apparatus for displaying and suggesting routes based on popularity of previously traveled routes and various other collected criteria corresponding with a user's desired route characteristic information, which may include selections and user profiles. This functionality enables enhanced situational awareness and increased confidence in suggested routes for users who prefer popular, frequently-traveled routes or privacy for users who prefer to avoid heavily-traveled routes.

Embodiments of the present technology provide a web server or other apparatus for providing route information to users via the Internet or other communications medium. The apparatus broadly includes computer readable memory and a processing device coupled with the memory. The memory may receive and store route data for a plurality of routes previously traveled by runners, bikers, and other users. The stored route data may include geographic locations of points along the routes, information relating to the number of times or how frequently users traveled through geographic locations associated with the routes, activity types associated with each of the routes, and dimensions corresponding to equipment used when the route was traveled. The processing device may display information about at least some of the stored routes and suggest one or more routes to users based on a comparison of the stored route data with one or more desired route characteristic information. In one embodiment, the processing device receives desired route characteristic information from a user, such as a desired activity type, and compares the desired route characteristic information with the stored route data to suggest at least one of the stored routes to the user based on the comparison. The processing device may also visually indicate a popularity of the stored and/or suggested routes with a color-coded heat map.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is therefore not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but not necessarily included. Thus, the present technology can include a variety of combinations and/or integrations of the embodiments described herein.

Embodiments of the present technology provide a web server or other apparatus that stores data associated with a plurality of routes previously traveled by a plurality of runners, bikers, or other users and suggests one or more stored routes to users based on a comparison of the stored route data with desired route characteristic information. The stored route data may include geographic locations of points along the routes, the number of times each of the routes was traveled by the plurality of users, and an indication of an activity type (e.g., running, cycling, boating, skating, etc.). An indication of a popularity of a route and/or geographic locations associated with a route may be provided on a display device. Conventional electronic devices and associated software programs enable a user to identify a route to travel based on fitness criteria and discrete geographic locations (e.g., geographic coordinates) that the user is interested in passing through. However, such conventional software programs do not suggest routes based on the popularity of a geographic location or stored route.

Runners and cyclists may prefer to run or bike along routes that are traveled frequently by others or avoid such frequently-traveled routes. For example, a user may desire to run or bike through geographic locations that have been previously traveled by other users. Users may also prefer to run or bike along routes that have been previously traveled by other users having equipment that is similar to the user's equipment. Similar preferences may be shared by users that will boat, roller skate, roller blade or skate board along a route. Thus, it may be desirable to suggest stored travel routes to users based on a comparison of desired route characteristic information with stored route data, which includes information relating to the number of times or how frequently users traveled a stored route or passed through geographic locations associated with a route.

The apparatus or web server may store route data received from multiple users and compare this information with a user's desired route characteristic information, such as desired activity type and various other preferences, to suggest at least one of the stored routes to the user. Based on this comparison, one or more routes of the plurality of stored routes may be suggested to the user and displayed on an electronic device of the user. For example, the one or more stored routes that are suggested to the user may be displayed on the user's electronic device in a color-coded heat map or in an ordered listing of the suggested routes, such that the user may easily identify stored routes best suited for the user's desired route characteristic information. In embodiments, the heat map may associate a distinguishable color with geographic locations associated with a stored route to indicate a frequency at which the geographic locations associated with the stored routes have been previously-traveled.

Figure 1:
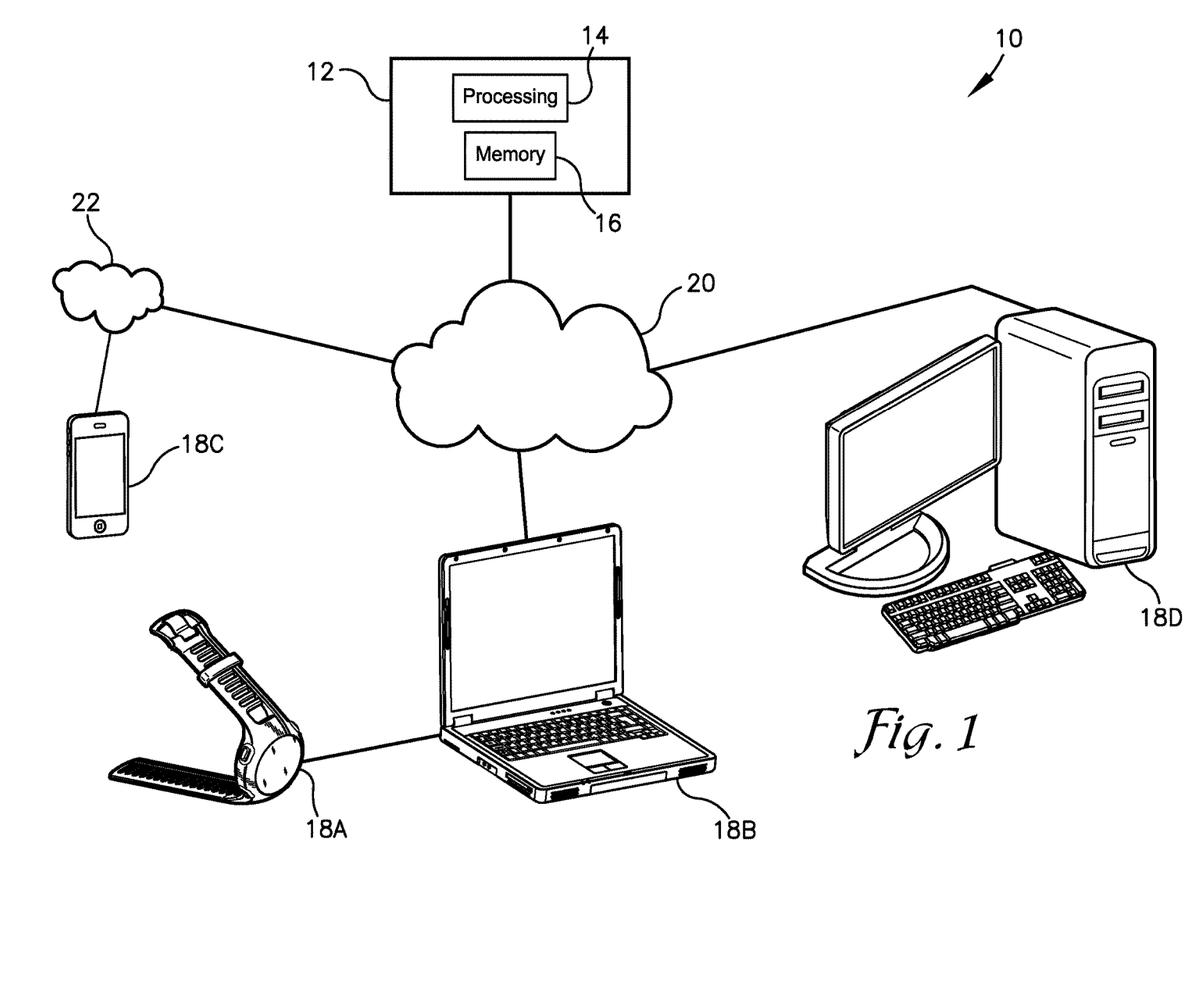
FIG. 1 is a schematic diagram of an exemplary computer and communication system that may be used to implement various embodiments of the present technology.

Embodiments of the technology will now be described in more detail with reference to the drawing figures. FIG. 1 illustrates an exemplary computer and communication system 10 that may be used to implement aspects of the technology discussed herein. The system 10 includes a web server or other electronic apparatus 12 having a processing device 14 and memory 16, as well as one or more computer programs for operating components of the system 10. The apparatus 12 may be accessed by one or more electronic devices 18A,B,C,D via a communications network 20 or a wireless network 22.

The apparatus 12 receives, stores, and provides access to the data and information described herein. The apparatus 12 may also implement one or more computer programs for performing some of the functions described herein and may provide a course file or a web-based portal that can be accessed by the electronic devices 18A,B,C,D and other such electronic devices. In some embodiments, the apparatus 12 may reside in a personal computer or server that is accessible by remote users via the Internet or other wired or wireless communication techniques. Embodiments of the apparatus 12 may include one or more servers running Windows; LAMP (Linux, Apache HTTP server, MySQL, and PHP/Perl/Python); Java; AJAX; NT; Novel Netware; Unix; or any other software system. The apparatus 12 includes or has access to computer memory, such as the memory 16, and other hardware, such as the processing device 14, and software for receiving, storing, accessing, and transmitting information as described below. The apparatus 12 may also include conventional web hosting operating software, searching algorithms, an Internet connection, and is assigned a URL and corresponding domain name so that it can be accessed via the Internet in a conventional manner In other embodiments, the apparatus 12 may be a personal computer, laptop, or any computing device operable to store information and execute software or computer codes associated with the procedures described herein.

The processing device 14 provides processing functionality for the apparatus 12 and may include any number of processors, microcontrollers, or other processing systems, and resident or external memory for storing data and other information accessed or generated by the apparatus 12. The processing device 14 may execute one or more software programs that implement the techniques and modules described herein. The processing device 14 is not limited by the materials from which it is formed or the processing mechanisms employed therein and, as such, may be implemented via semiconductor(s) and/or transistors (e.g., electronic integrated circuits (ICs)), and so forth.

The memory 16 is an example of device-readable storage media that provides storage functionality to store various data associated with the operation of the computer system 12, such as the software program and code segments mentioned above, or other data to instruct the processing device 14 and other elements of the computer system 12 to perform the techniques described herein. Although a single memory 16 is shown, a wide variety of types and combinations of memory may be employed. The memory 16 may be integral with the processing device 14, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

Figure 2:
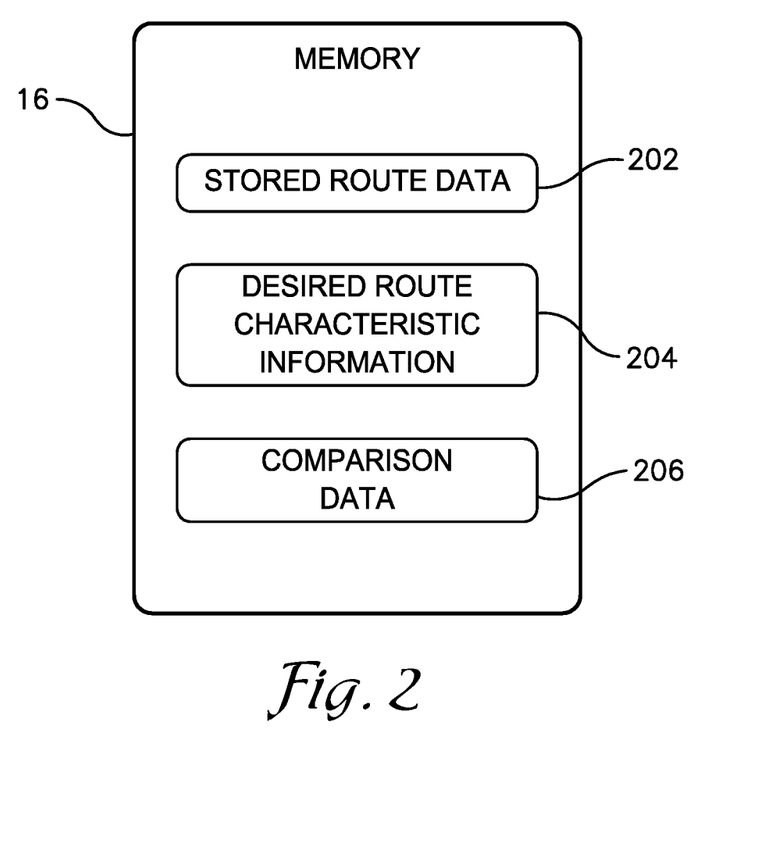
FIG. 2 is a schematic block diagram of various data stored in memory of a web server or apparatus of FIG. 1.

The memory 16 of the web server or other electronic apparatus 12 receives and stores route data for a plurality of routes taken by a plurality of users of electronic devices 18A,B,C,D, as illustrated in FIG. 2 as stored route data 202. The memory 16 may also include desired route characteristic information 204 from the user, which may be a desired activity type (e.g., running, cycling, boating, skating, etc.), desired geographic area, type of electronic device the user intends to use while traveling a route, the dimensions corresponding to equipment of the user, or selection of another user who has provided route data. Memory 16 may also include comparison data 206 determined based on a comparison of the stored route data 202 and the desired route characteristic information 204, as described in detail below.

The electronic devices 18A,B,C,D may be any computing devices used by users for sending and/or receiving route data and other information described herein. The electronic devices 18A,B,C,D may be desktop computers, laptop computers, tablet computers, portable navigation devices (PND), mobile phones, personal digital assistants, fitness tracking devices, multimedia devices, media players, game devices, combinations thereof, and so forth. In particular embodiments, the devices 18A,B,C,D may include, for example, a cycle computer, a sport watch, a golf computer, a smart phone providing fitness or sporting applications (apps), a hand-held GPS device used for hiking, and so forth. Each personal computing device 18A,B,C,D preferably includes or can access an Internet browser and a conventional Internet connection such as a wireless broadband connection, DSL converter, or ISDN converter so that it can exchange data with the computer system 12 via the communications network 20. One or more of the devices 18A,B,C,D may also exchange data with another one of the devices 18A,B,C,D via a wired or wireless data link as illustrated. For example, a fitness watch 18A may be operable to interface with a laptop 18B to send and receive route information and user characteristics, as described herein.

The communications network 20 may be the Internet or any other communications network such as a local area network, a wide area network, or an intranet. The communications network 20 may include or be in communication with a wireless network 22 capable of supporting wireless communications such as the wireless networks operated by AT&T, Verizon, or Sprint. The wireless network 22 may include conventional switching and routing equipment. The communications network 20 and wireless network 22 may also be combined or implemented with several different networks.

The networks 20 and 22 described above are representative of a variety of different communication pathways and network connections which may be employed, individually or in combinations, to communicate among the components of the system 10. Thus, the networks 20 and 22 may be representative of communication pathways achieved using a single network or multiple networks. Further, the networks 20 and 22 are representative of a variety of different types of networks and connections that are contemplated including, but not limited to: the Internet; an intranet; a satellite network; a cellular network; a mobile data network; wired and/or wireless connections; and so forth.

Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth.

The components of the system 10 illustrated and described herein are merely examples of equipment that may be used to implement embodiments of the present invention and may be replaced with other equipment without departing from the scope of the present invention. Some of the illustrated components of the system 10 may also be combined and/or omitted.

Embodiments of the present technology may also comprise one or more computer programs stored in or on computer-readable medium residing on or accessible by the computer system 12 or the electronic devices 18A,B,C,D. The computer programs may comprise listings of executable instructions for implementing logical functions in the processing device 14 and/or the electronic devices 18A,B,C,D and can be embodied in any non-transitory computer-readable medium, such as the memory 16, for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can contain, store, or communicate the programs. The computer-readable medium can be, for example, but not limited to, an electronic, magnetic, optical, electro-magnetic, infrared, or semiconductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

Figure 3:
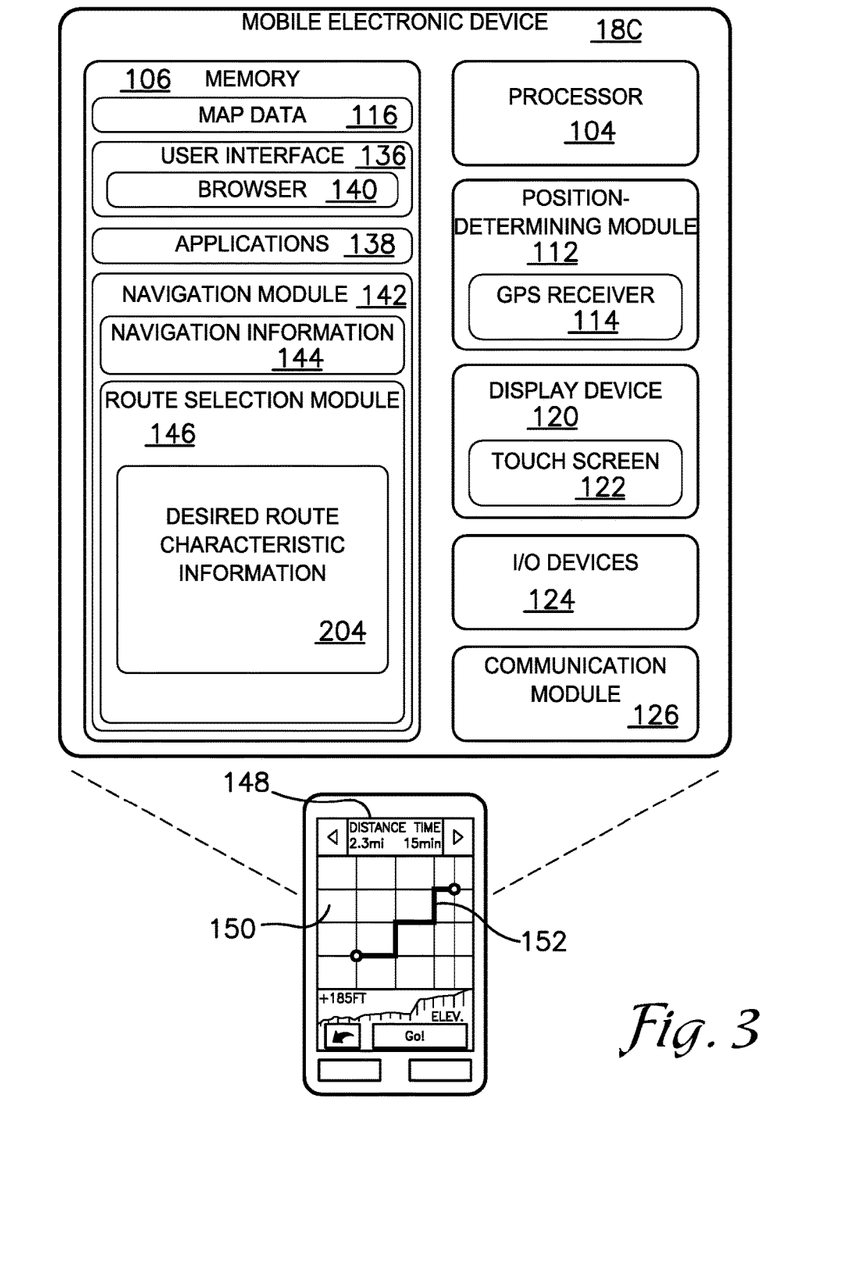
FIG. 3 is a schematic block diagram illustrating the functional components of an electronic device of FIG. 1.

FIG. 3 illustrates one of the electronic devices 18C in more detail. Specifically, mobile electronic device 18C is operable to provide navigation functionality to a user thereof using various components of the system 10 illustrated in FIG. 1 and described herein. The mobile electronic device 18C may be configured in a variety of ways. For instance, the mobile electronic device 18C may be configured for use during fitness and/or sporting activities and comprise a cycle computer, a sport watch, a golf computer, a smart phone providing fitness or sporting applications (apps), a hand-held GPS device used for hiking, and so forth. However, it is contemplated that the techniques of the present technology may be implemented in any mobile electronic device that includes navigation functionality. In the following description, a referenced component, such as mobile electronic device 18C, may refer to one or more entities, and therefore by convention reference may be made to a single entity (e.g., the mobile electronic device 18C) or multiple entities (e.g., the mobile electronic devices 18C, the plurality of mobile electronic devices 18C, and so on) using the same reference number.

In FIG. 3, the mobile electronic device 18C is illustrated as including a processor 104 and a memory 106. The processor 104 provides processing functionality for the mobile electronic device 18C and may include any number of processors, microcontrollers, or other processing systems, and resident or external memory for storing data and other information accessed or generated by the mobile electronic device 18C. The processor 104 may execute one or more software programs that implement the techniques and modules described herein. The processor 104 is not limited by the materials from which it is formed or the processing mechanisms employed therein and, as such, may be implemented via semiconductor(s) and/or transistors (e.g., electronic integrated circuits (ICs)), and so forth.

The memory 106 is an example of device-readable storage media that provides storage functionality to store various data associated with the operation of the mobile electronic device 18C, such as the software program and code segments mentioned above, or other data to instruct the processor 104 and other elements of the mobile electronic device 18C to perform the techniques described herein. Although a single memory 106 is shown, a wide variety of types and combinations of memory may be employed. The memory 106 may be integral with the processor 104, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

Figure 4:
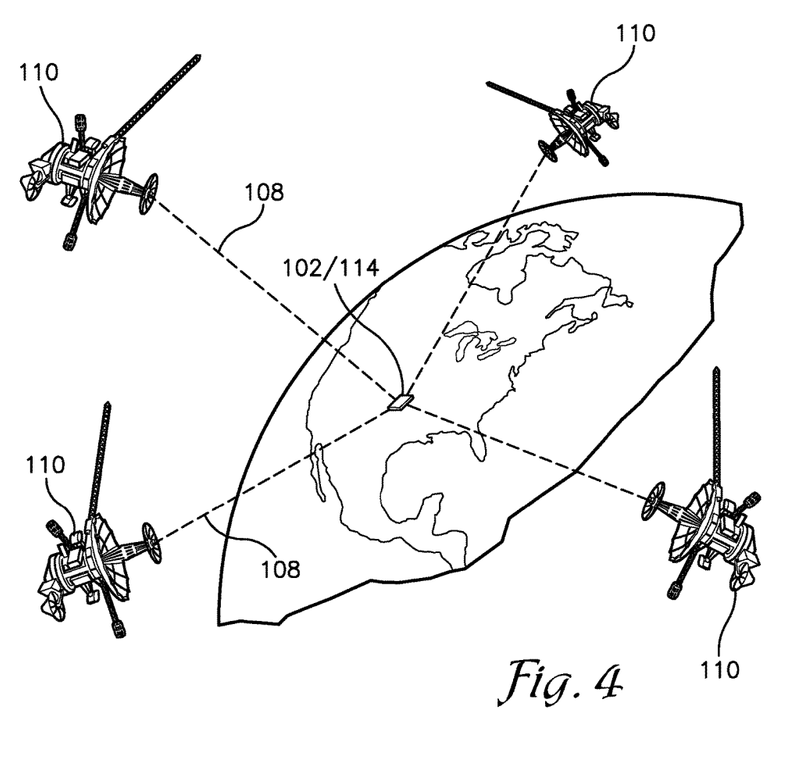
FIG. 4 is a schematic diagram of a Global Positioning System (GPS) that may be used by various embodiments of the invention.

The mobile electronic device 18C is further illustrated as including functionality to determine its geographic location. For example, mobile electronic device 18C may receive signal data 108 transmitted by one or more position data platforms and/or position data transmitters, examples of which are depicted as the GPS satellites 110 in FIG. 4. More particularly, mobile electronic device 18C may include a position-determining module 112, as illustrated in FIG. 3, that may manage and process signal data 108 received from Global Positioning System (GPS) satellites 110 via a GPS receiver 114. The position-determining module 112 is representative of functionality operable to determine a geographic position through processing of the received signal data 108. The signal data 108 may include various data suitable for use in position determination, such as timing signals, ranging signals, ephemerides, almanacs, and so forth.

Position-determining module 112 may also be configured to provide a variety of other position-determining functionality. Position-determining functionality, for purposes of discussion herein, may relate to a variety of different navigation techniques and other techniques that may be supported by "knowing" one or more positions. For instance, position-determining functionality may be employed to provide position/location information, timing information, speed information, and a variety of other navigation-related data. Accordingly, the position-determining module 112 may be configured in a variety of ways to perform a wide variety of functions. For example, the position-determining module 112 may be configured for outdoor navigation, vehicle navigation, aerial navigation (e.g., for airplanes, helicopters), marine navigation, personal use (e.g., as a part of fitness-related equipment), and so forth. Accordingly, the position- determining module 112 may include a variety of devices to determine position using one or more of the techniques previously described.

The position-determining module 112, for instance, may use signal data 108 received via the GPS receiver 114 in combination with map data 116 that is stored in the memory 106 and/or otherwise received by the mobile electronic device 18C to generate navigation instructions (e.g., turn-by-turn instructions to an input destination or POI), show a current position on a map, and so on. Position-determining module 112 may include one or more antennas to receive signal data 108 as well as to perform other communications, such as communication via one or more networks 20,22 described herein. The position-determining module 112 may also provide other position-determining functionality, such as to determine an average speed, calculate an arrival time, and so on.

Although a GPS system is described and illustrated in relation to FIGS. 2 and 3, it should be apparent that a wide variety of other positioning systems may also be employed, such as other global navigation satellite systems (GNSS), terrestrial based systems (e.g., wireless-phone based systems that broadcast position data from cellular towers), wireless networks that transmit positioning signals, and so on. For example, positioning- determining functionality may be implemented through the use of a server in a server- based architecture, from a ground-based infrastructure, through one or more sensors (e.g., gyros, odometers, and magnetometers), use of "dead reckoning" techniques, and so on.

The mobile electronic device 18C includes a display 120 to display information to a user of the mobile electronic device 18C. In embodiments, the display 120 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display 120 may be backlit via a backlight such that it may be viewed in the dark or other low-light environments.

The display 120 may be provided with a touch screen 122 to receive input (e.g., data, commands, etc.) from a user. For example, a user may operate the mobile electronic device 18C by touching the touch screen 122 and/or by performing gestures on the screen 122. In some embodiments, the touch screen 122 may be a capacitive touch screen, a resistive touch screen, an infrared touch screen, combinations thereof, and the like. The mobile electronic device 18C may further include one or more input/output (I/O) devices 124 (e.g., a keypad, buttons, a wireless input device, a thumbwheel input device, a trackstick input device, and so on). The I/O devices 124 may include one or more audio I/O devices, such as a microphone, speakers, and so on.

The mobile electronic device 18C may also include a communication module 126 representative of communication functionality to permit mobile electronic device 18C to send/receive data between different devices (e.g., components/peripherals) and/or over the one or more networks 20 and 22 described above. Communication module 126 may be representative of a variety of communication components and functionality including, but not limited to: one or more antennas; a browser; a transmitter and/or receiver; a wireless radio; data ports; software interfaces and drivers; networking interfaces; data processing components; and so forth.

The mobile electronic device 18C through functionality represented by the communication module 126 may be configured to communicate, via one or more of the networks 20,22 described above, with a cellular provider and an Internet provider to receive mobile phone service and various content, respectively. Content may represent a variety of different content, examples of which include, but are not limited to: map data, which may include route information, route popularity, and the like; fitness metrics, such as heart rate, speed, and the like; dimensions and characteristics relating to an activity, such as activity type and details associated with equipment used to travel along a route (e.g., dimensions of exercise equipment, watercraft, aircraft, automobile, motorcycle, etc.); web pages; services; music; photographs; video; email service; instant messaging; device drivers; real-time and/or historical weather data; instruction updates; and so forth.

The mobile electronic device 18C is illustrated as including a user interface 136, which is storable in memory 106 and executable by the processor 104. The user interface 138 is representative of functionality to control the display of information and data to the user of the mobile electronic device 18C via the display 120. In some implementations, the display 120 may not be integrated into the mobile electronic device 18C and may instead be connected externally using universal serial bus (USB), Ethernet, serial connections, and so forth. The user interface 136 may provide functionality to allow the user to interact with one or more applications 138 of the mobile electronic device 18C by providing inputs via the touch screen 122 and/or the I/O devices 124. For example, the user interface 136 may cause an application programming interface (API) to be generated to expose functionality to an application 138 to configure the application for display by the display 120 or in combination with another display. In embodiments, the API may further expose functionality to configure the application 138 to allow the user to interact with an application by providing inputs via the touch screen 122 and/or the I/O devices 124.

Applications 138 may comprise software, which is storable in memory 106 and executable by the processor 104, to perform a specific operation or group of operations to furnish functionality to the mobile electronic device 18C. Example applications may include fitness application, exercise applications, health applications, diet applications, cellular telephone applications, instant messaging applications, email applications, photograph sharing applications, calendar applications, address book applications, and so forth.

The user interface 136 may also include or have access to a browser 140. The browser 140 enables the mobile electronic device 18C to display and interact with content such as a webpage within the World Wide Web, a webpage provided by a web server in a private network, and so forth. The browser 140 may be configured in a variety of ways. For example, the browser 140 may be configured as an application 138 accessed by the user interface 136. The browser 140 may be a web browser suitable for use by a full resource device with substantial memory and processor resources (e.g., a smart phone, a personal digital assistant (PDA), etc.). However, in one or more implementations, the browser 140 may be a mobile browser suitable for use by a low- resource device with limited memory and/or processing resources (e.g., a mobile telephone, a portable music device, a transportable entertainment device, etc.). Such mobile browsers typically conserve memory and processor resources, but may offer fewer browser functions than web browsers.

The mobile electronic device 18C is illustrated as including a navigation module 142, which is storable in memory 106 and executable by the processor 104. The navigation module 142 represents functionality to access map data 116 that is stored in the memory 106 or otherwise accessed by the mobile electronic device 18C to provide mapping and navigation functionality to the user of the mobile electronic device 18C. For example, the navigation module 142 may generate navigation information that includes maps and/or map-related content for display by display 120. As used herein, map related content includes information associated with maps generated by the navigation module 142 and may include route information, POIs, information associated with POIs, map legends, controls for manipulation of a map (e.g., scroll, pan, etc.), street views, aerial/satellite views, and the like, displayed on or as a supplement to one or more maps.

In one or more implementations, the navigation module 142 is configured to utilize the map data 116 to generate navigation information 144 that includes maps and/or map-related content for display by the mobile electronic device 18C independently of content sources external to the mobile electronic device 18C. Thus, for example, the navigation module 142 may be capable of providing mapping and navigation functionality when access to external content is not available through network 20,22. It is contemplated; however, that the navigation module 142 may also be capable of accessing a variety of content via the networks 20,22 to generate navigation information including maps and/or map-related content for display by the mobile electronic device 18C in one or more implementations.

The navigation module 142 may be configured in a variety of ways. For example, the navigation module 142 may be configured as an application 138 accessed by the user interface 136. The navigation module 142 may utilize position data determined by the position-determining module 112 to show a current position of the user (e.g., the mobile electronic device 18C) on a displayed map, furnish navigation instructions (e.g., turn-by-turn instructions to an input destination or POI), calculate traveling distances and times, and so on.

As illustrated in FIG. 3, the navigation module 142 further includes a route selection module 146, which is also storable in memory 106 and executable by the processor 104. The route selection module 146 causes the display 120 of the mobile electronic device 18C to be configured to display suggested route information 148. In the implementation shown, the route selection information 148 is illustrated in the format of a map page 150 that includes a route graphic 152 representing a suggested route that may be traversed by a user of the mobile electronic device 18C. In some embodiments of the invention, the route selection module 146 may include information relating to the desired route characteristic information 204 associated with the user, as described herein. However, note that the desired route characteristic information 204 may also be collected and/or stored in memory 16 as described herein and illustrated in FIG. 2.

In embodiments, a remote web server or other electronic apparatus 12 may provide route selection module 146 of mobile electronic device 18C information associated with a suggested route, such as suggested route information 148. For example, a suggested route may be provided to the user of mobile electronic device 18C in a course file, such as TPX, GPX, FIT, or KML files, or via a web browser displayed on the display 120 of mobile electronic device 18C. The course files may be provided by the remote web server or other electronic apparatus 12 to various electronic devices 18A,B,C,D. For example, the course files may be stored in memory 106 of mobile electronic device 18C and may contain map data and/or navigation data associated with the suggested route to assist the user in navigating the route.

An exemplary procedure for assisting a user in selecting a route on which to run, bike, or perform other activity, based on comparing desired route characteristic information 204 with tracked popularity of routes traveled by other users is described herein. The procedure may broadly include receiving and storing route data for routes previously traveled by a plurality of users, receiving desired route characteristic information 204 from the user, comparing the desired route characteristic information 204 to the stored route data 202, and suggesting at least one of the stored routes to the user based on the comparison. Furthermore, the procedure may include visually indicating with a color-coded heat map a popularity of all stored routes or the stored routes suggested to the user based on the comparison.

Figure 5:
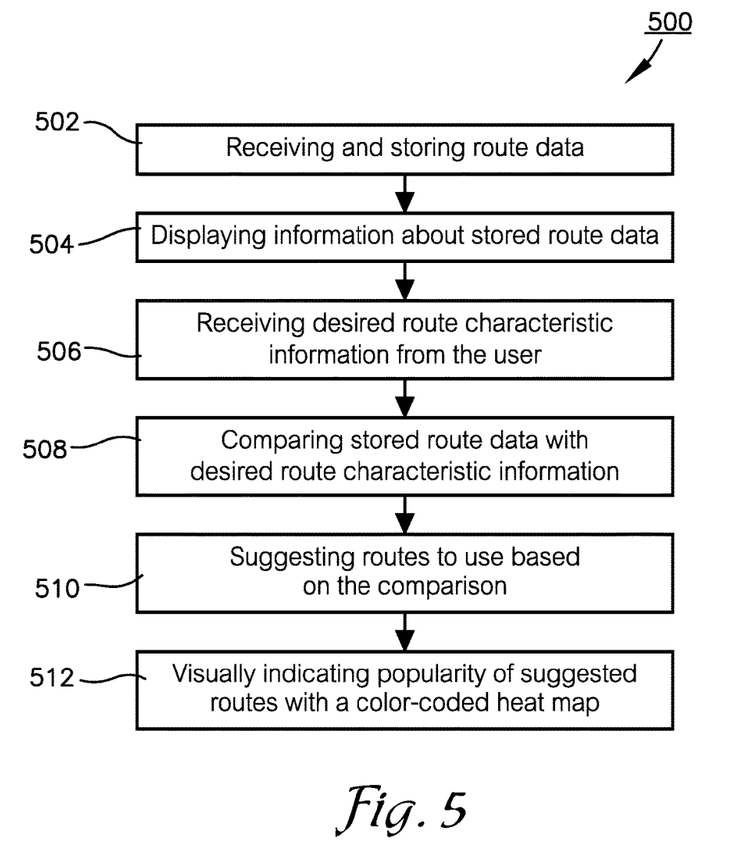
FIG. 5 is a flow chart of an exemplary procedure for providing route information to users in accordance with embodiments of the present technology.

The flow chart of FIG. 5 depicts the steps of an exemplary procedure 500 for providing route information to the user for selecting a route. In some alternative implementations, the functions noted in the various blocks may occur out of the order depicted in FIG. 5. For example, two blocks shown in succession in FIG. 5 may in fact be executed substantially concurrently, or the blocks may sometimes be executed in the reverse order depending upon the functionality involved.

The procedure 500 may comprise the step of receiving and storing route data associated with routes previously traveled by a plurality of users, as depicted in block 502. For example, the stored route data 202 may be received and stored in the memory 16 of the apparatus 12 described above. The route data may be collected from electronic devices, such as electronic device A,B,C,D described above, and/or entered manually by one or more of the users submitting route data. The stored route data 202 may include geographic locations of points on the routes traveled by the users, types of electronic devices used to collect geographic locations of points along the traveled routes, type(s) of activity associated with each of the routes, characteristics and dimensions associated with the user's equipment, types of activity, and the like, and/or the number of times each route was traveled by the plurality of users. The types of activity associated with the routes may include running, cycling, skating, and the like. Characteristics and dimensions associated with the types of activities may depend on exercise equipment or vehicles used to travel the routes. For example, characteristics and dimensions associated with exercise equipment may include dimensions of bicycles, roller blades, skateboards, and vehicles, such as a watercraft, aircraft, automobile, motorcycle, and the like. The number of times each route was traveled by the plurality of users may be used to determine a frequency at which the geographic locations associated with the stored routes have been previously-traveled by users. A popularity of a route may be determined based on the number of times each route was traveled and/or the frequency at which the routes have been previously-traveled.

The route data may further include or be categorized according to time, day, month, season, tides, types of electronic devices, types of activity, and/or characteristics and dimensions of equipment used to travel the routes by the users from which route data is collected. In embodiments, the popularity of stored route data 202 may be determined and indicated based on the time, day, month, season, tides, types of electronic devices, types of activity, or dimensions corresponding to equipment used to travel the stored routes. Route data may also include information associated with the users being tracked or inputting route data into the apparatus 12, such as the type of travel or exercise equipment used, type of activity performed, and teams or groups with which the person is associated. For example, the stored route data 202 may include an identification of the users who traveled each of the routes and the desired route characteristic information 204 may identify a selected user. In embodiments, the processing device 14 suggests to the user who provided the desired route characteristic information 204 one or more stored routes that were previously traveled by the selected user. The stored route data 202 may also include fitness metrics associated with the user at various geographic locations through which the user traveled while wearing or holding a mobile electronic device.

The procedure 500 may further include the step of displaying information about the routes previously taken by some or all of the users, as depicted in block 504. For example, the processing device 14 may display or provide information to display an indication of popularity of routes, geographic locations of points of interest, starting points of routes, types of activities associated with the routes, types of equipment used to travel the routes, and any other route data described herein. Popularity of the routes may be determined by the processing device 14 using the stored route data 202. The number of times each route was traveled by the plurality of users may be used to determine the popularity of stored routes that have been previously-traveled by some or all of the users. For example, the frequency at which the routes have been previously-traveled may be used to determine the popularity of stored routes. In embodiments, the popularity of stored routes may be presented in the form a listing ranking each route by its popularity. Displaying information about the routes may be accomplished via an Internet portal on one of the electronic devices 18A,B,C,D.

The procedure 500 may also include the step of receiving desired route characteristic information 204 from a user wishing to receive route instructions, as depicted in block 506. The desired route characteristic information 204 may be based on user selections made via the electronic device, a profile created by or for the user, or other various sensed information about the user communicated to the processing device 14. For example, the user's desired route characteristic information 204 may be input or selected via a software program or app on the electronic device 18A,B,C,D or via an Internet portal accessed and displayed by the electronic device 18A,B,C,D. The user's desired route characteristic information 204 may be uploaded to the apparatus 12 and stored on the memory 16 via communications network 20 or wireless network 22. In some embodiments, the user's desired route characteristic information 204 may be stored in memory 16 and memory 106 as a user profile which may be completed and edited by the user via the electronic device 18A,B,C,D.

The user's desired route characteristic information 204 may include the user's name, desired activity type, a type of electronic device associated with or in use by the user, selected equipment for the user's desired activity type, characteristics and dimensions corresponding to the selected equipment, a geographic area associated with and/or selected by the user, and/or one or more users (e.g., a group, team, or individuals) associated with the user. The user's desired route characteristic information may also include user preferences such as a desired level of route popularity and a time, day, month, or season at which the user will perform the desired activity type. The user's desired activity type may include running, cycling, boating, roller skating, roller blading, skateboarding, and the like. Furthermore, the user's activity type may include subcategories of activity types, such as street biking versus mountain biking. The user's selected equipment may include bikes, skates, skateboards, boats, other exercise equipment, vehicles, and the like. The user's selected equipment may include specific dimensions that enable enhanced situational awareness and increased confidence in suggested routes for users who prefer popular, frequently-traveled routes by other users have equipment of similar size and capability. For example, a user may select a boat having precise width, height above water and depth below water to locate previously-traveled routes by other users having a boat that similar to or exceeding the dimensions of the user's boat. Knowing that other users with similar equipment have safely traveled along a route in a body of water may provide the user with enhanced situational awareness and increased confidence to travel through that body of water. Furthermore, the user's selected equipment may include specific types, brands, models, or sizes of the equipment listed herein, such as a specific type of bike.

The procedure 500 may also include the steps of comparing the route data and the desired route characteristic information 204, as depicted in block 508, and suggesting one or more stored routes to the user based on the comparison, as depicted in block 510. For example, previously-traveled routes may be suggested to the user based on a user-specified geographic area, an activity type (running, cycling, etc.), user-selected equipment, and/or desired popularity of a route. A determination of popularity of the routes and/or geographic locations along the routes may be accomplished by analyzing the route data described above. For example, the processing device 14 may access the stored routes and determine an extent to which a route has been traveled or a geographic location has been visited based on a count of a total number of times each route was previously traveled or a count of a total number of times a route associated with each geographic location was traveled. The processing device 14 may also determine if users that traveled a particular route took that route multiple times (e.g., whether a few users took the route many times or many users took the route a few times). Another factor used to determine the popularity of a route may be the frequency of which the route is traveled by users (e.g., multiple times a day, a few times a month, etc.).

The popularity of a route may be communicated to the user by providing data representative of a total number of times geographic locations comprising the route were traveled within a relevant time period or by categorizing each route into a set of ranges. For example, in one embodiment, a set of five ranges may be used to indicate the popularity of previously traveled routes. A first range may be associated with most-heavily-traveled routes (e.g., routes that rank in the 80-100$^{th}$ percentile of stored routes, 80-100% of users tracked previously traveled these routes, etc.). A second range may be associated with heavily-traveled routes (e.g., routes rank in the 60-79$^{th}$ percentile of stored routes, 60-79% of users tracked previously traveled these routes, etc.). A third range may be associated with routes of medium use (e.g., routes rank in the 40-59$^{th}$ percentile of stored routes, 40-59% of users tracked previously traveled these routes, etc.). A fourth range may be associated with lightly-traveled routes (e.g., routes rank in the 20-39$^{th}$ percentile of stored routes, 20-39% of users tracked previously traveled these routes, etc.). A fifth range may be associated with rarely-traveled routes (e.g., routes rank at or less than the 19$^{th}$ percentile of stored paths, 19% or less of users tracked previously traveled these routes, etc.). This evaluation technique may be applied to each stored route independent of the geographic locations comprising each route, based on the geographic locations comprising each route, or combinations thereof. In embodiments, a color-coded heat map may associate a distinguishable color with each popularity range and present each route in one of five colors on a map. These ranges are only examples and may be replaced with any other ranges without departing from the scope of the present technology.

Comparisons of the route data and desired route characteristic information 204 may be accomplished using a variety of techniques. For example, the processing device 14 may analyze the stored route data 202 to identify geographic locations or routes that are heavily traveled in the morning, afternoon, or evening hours, or that are more popular during a particular season. This may enable the user to select or input desired route characteristic information 204 and join others on a route at a time when it is heavily traveled or to pick a time of day that it is not heavily traveled to avoid the increased activity in those geographic locations. Furthermore, tide related information may be selected or inputted by the user as desired route characteristic information 204 to identify areas of a route affected by the tide at a particular time of day or time of year.

In other embodiments, the comparison may include comparing types of activity and the exercise equipment or vehicle used to travel the stored route with a desired activity type and various characteristics and/or dimensions of exercise equipment or vehicles selected or input by the user as desired route characteristic information 204. Specifically, if the user plans to travel a route using particular fitness equipment or a particular vehicle, the processing device 14 may compare the desired route characteristic information 204 with the stored route data 202 to determine which stored routes were previously traveled using the same equipment or vehicle, or which stored routes were previously traveled using equipment or vehicles having similar characteristics or dimensions and suggest one or more of the stored routes to the user. The user's fitness equipment or vehicle may be provided to the apparatus 12 via a user profile, user selection of particular fitness equipment or vehicles, or manual input by the user of particular characteristics or dimensions of the fitness equipment or vehicle that will be used to travel a suggest route. For example, if the user is interested in using a bicycle to travel to a destination or perform a workout, routes or geographic locations previously traveled by other users using bicycles may be suggested and displayed. This functionality may also allow the user to identify the popularity of routes or geographic locations for a particular activity type or by a particular fitness equipment or vehicle in order to select a route for travel based on the user's interest in travelling through popular geographic locations. For example, a runner may desire to run on a path that is accessible to bicycles, but not frequently traveled by others on bicycles to avoid incidents or traffic along the suggested route. Similarly, fisherman can identify heavily traveled areas of a body of water and receive suggested routes that may avoids fishing in those areas or identify a suggested route that is not popular for other users.

In some embodiments of the technology, the fitness equipment or vehicle characteristics or dimensions may be specified by the user as desired route characteristic information 204 if the user is interested in using a boat having known characteristics or dimensions to travel along a suggested route to a destination, such as a port, diving location, and the like. In this case, the apparatus 12 may suggest one or more routes previously traveled by similar types and sizes of boats. This suggestion may allow the user, such as a watercraft operator, to identify popular routes or waterways navigated by other similar types of watercraft and select a suggested route for travel based on the popularity of the stored routes. The user may also identify popular routes through a geographic location such as a port or a coral reef and determine routes, courses, and areas of interest for a particular activity type, such as areas popular for fishing or diving, and select a suggested route for travel based on the popularity of the stored routes. The user may also identify areas having sufficient width, depth, draft, and clearance for the user's particular boat or watercraft and select a suggested route for travel based on the popularity of the stored routes. The similarity between the user's electronic device, which may be input as desired route characteristic information 204, and the types of electronic devices used to gather the stored route data 202 may also be used in a comparison to suggest one or more routes to a user and assist the user in determining which stored route to follow.

In another embodiment of the present technology, the apparatus 12 may enable a driver interested in traveling along a stored route to a destination using an automobile to identify tourist areas and paths of sufficient width to drive through with a vehicle selected by the user. In yet another embodiment of the present technology, the apparatus 12 may enable pilots interested in flying along a stored route to a destination in an aircraft to identify popular flight paths for other users. For example, a pilot interested in flying to a destination through a mountainous terrain can have increased confidence for a route through the mountains if it has been frequently traveled by other pilots in similar aircraft, time of day, or other desired route characteristic information 204.

Finally, the procedure 500 may include the step of visually indicating popularity of the routes suggested to the user on a display of the electronic device, such as with a color-coded heat map and/or an ordered listing of routes, as depicted in block 512. This may enable the user to easily select a route or geographic location of interest based on popularity of suggested routes and/or geographic locations. Specifically, the heat map may communicate the popularity of a previously-traveled route or geographic location has been traveled by other users by associating a distinguishable color with each stored route or geographic location. Associating distinguishable colors with the geographic locations associated with displayed routes may indicate a frequency at which the geographic locations have been previously-traveled. The suggestion of a stored route may be based on the popularity of the routes or independent of the popularity of the routes. Thus, viewing a color-coded heat map may enable a user to select a suggested route because this color-coding functionality helps distinguish a heavily-traveled route from a lightly-traveled route when multiple paths are simultaneously present and/or suggested by the computer program or apparatus 12.

Figure 6:
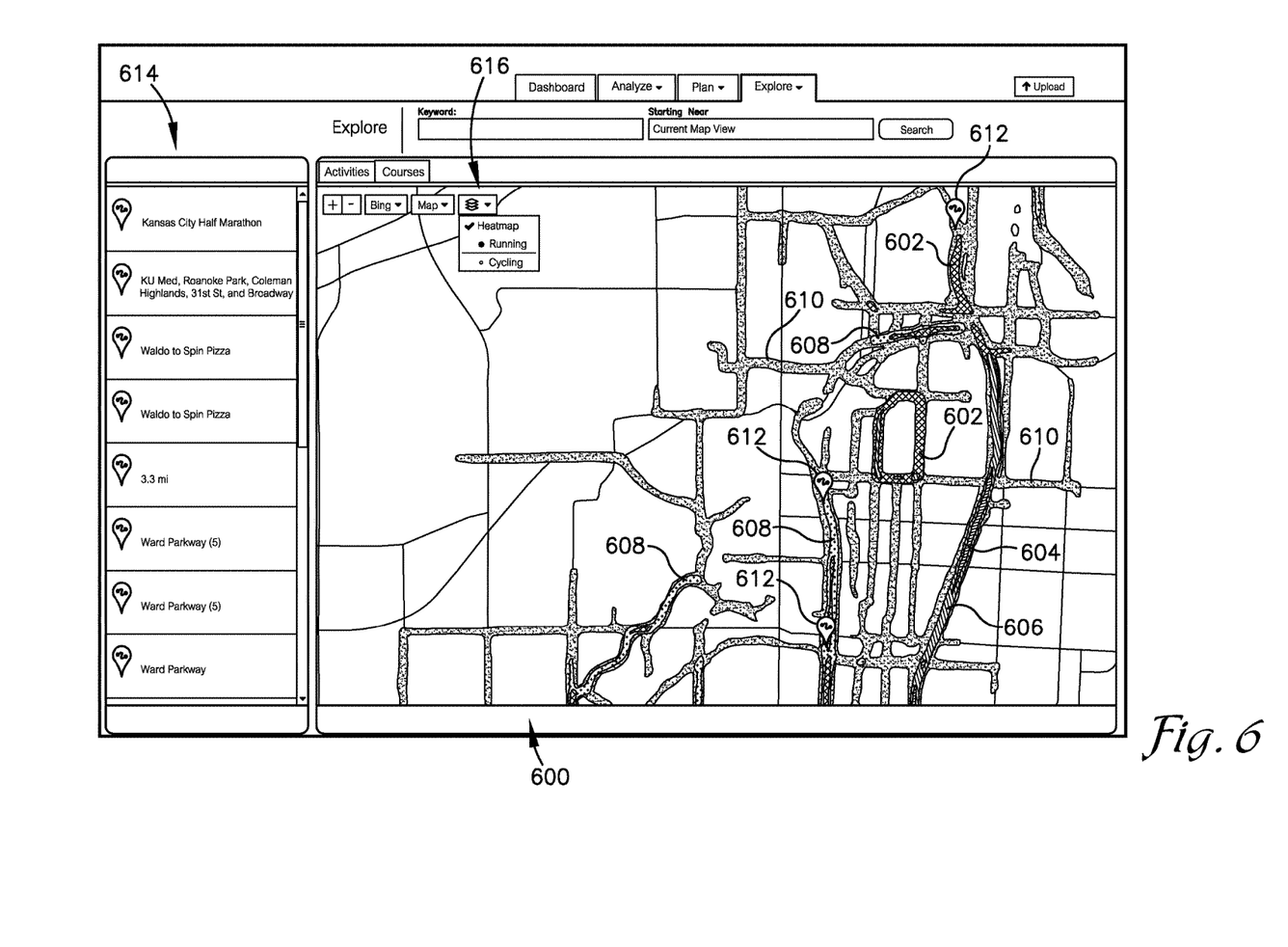
FIG. 6 is an exemplary screen shot of a display of the electronic device of FIG. 3.

As illustrated in FIG. 6, the heat map 600 may be provided via a Web portal accessible by the user's electronic device 18A,B,C,D and may display a plurality of distinguishable colors associated with a stored route or geographic locations associated with a route within a region being presented in the heat map. For example, the geographic locations associated with a highly-traveled route may be color-coded red, as represented by the cross-hatching 602 on the heat map 600, while moderately highly-traveled geographic locations or routes may be color-coded orange, as represented by the cross-hatching 604, medium-traveled geographic locations or routes may be color-coded yellow, as represented by the cross-hatching 606, occasionally-traveled geographic locations or routes may be color-coded green, as represented by the cross-hatching 608, and rarely-traveled geographic locations or routes may be color-coded blue, as represented by the cross-hatching 610. As described above, a color-coded heat map may associate a distinguishable color with a popularity range and present each route in one of a plurality of colors on a map.

The heat map 600 may enable the user to identify the popularity of running and cycling workout hot spots in a region, such as a city park. Such popularity of use information may help the user find new locations to work out, create a new course, see where they may be near other runners, or suggest a good location to meet up with friends. Routes suggested to the user may be visually indicated on a color-coded heat map associating a distinguishable color with geographic locations associated with the stored routes to indicate a frequency at which the geographic locations have been previously traveled. In some embodiments of the technology, a team of cyclists or runners that are not able to practice navigating a route together may identify routes that have been previously traveled by teammates and travel the more popular routes for practice. Specifically, routes suggested to the user may be filtered based on routes previously-traveled by teammates or group members associated with the user.

The heat map 600 may also include start point graphics 612 indicating the start and/or finishing point of a particular route. Furthermore, a listing 614 of the routes may be provided and may be ranked by popularity of the routes or any other criteria selected by the user. For example, if a user profile indicates that the user prefers to run alone, routes may be displayed in reverse order from least to most popular and may be filtered according to routes collected from other runners only and could further be filtered by a time of day that the user wishes to run. Also, as illustrated in FIG. 6, drop down menus 616 or other selectable options may be provided to the user in order to input desired route characteristic information 204. For example, a drop down menu 616 may enable a user to select the user's desired activity type, such as running or cycling. Then the stored routes displayed on the heat map 600 and in the listing 614 may be filtered according to the selected activity type. The stored routes that are displayed may be suggested for the user based on a comparison of at least some of the user's desired route characteristic information 204 with the stored route data 202 or present all stored routes for a displayed geographic region.

In embodiments, a desired geographic area or level of zoom applied to the heat map 600 may be considered desired route characteristic information 204 herein and may be used as criteria to filter which of the stored routes will be displayed on the heat map 600 and/or listing 614. In some embodiments of the technology, the popularity of a route may be scaled according to a level of zoom. For example, the number of times required for a route to be presented in a heat map covering a large geographic area may be much greater than the number of times required for that route to appear in a heat map of a much smaller geographic area.

In some embodiments of the technology, the heat map 600 and/or the suggested routes described herein may be provided to the user via course files, such as TPX, GPX, FIT, or KML files. The course files can be downloaded to various electronic devices, such as the fitness watch illustrated in FIG. 1. The course files may contain map data and/or navigation data to assist the user in navigating the route using the user's selected electronic device. In some instances, the course files may also contain and/or keep track of various fitness metrics, such as heart rate, speed, and the like.

The above-mentioned identification of route and geographic location usage may be applied to any situation in which position locations are stored (e.g., tracklogs) and used. The apparatus 12 may suggest and enable users to identify popular and heavily-traveled routes and geographic locations for fitness, recreational, marine, aviation, and/or automotive uses.

Although the technology has been described with reference to the embodiments illustrated in the attached drawing figures, it is noted that equivalents may be employed and substitutions made herein without departing from the scope of the technology as recited in the claims.

What is claimed is:

1. An apparatus for providing route information to a user, the apparatus comprising:
   a non-transitory computer readable memory storing information associated with the user's boat and route data for a plurality of routes previously traveled by a plurality of users on a boat, the stored route data including geographic locations of points along the routes, information relating to the number of times or how frequently the users traveled the routes or passed through the geographic locations of points along the routes, and information associated with the boat used to travel the routes; and
   a processing device coupled with the memory and configured to
      display information about at least some of the stored routes previously traveled on a boat by users, receive information associated with the user's boat from the user, compare the information associated with the user's boat with the stored route data, suggest at least one of the stored routes to the user based on the comparison, and visually indicate with a color-coded heat map a popularity of the suggested routes, the heat map associating a distinguishable color with geographic locations associated with the stored routes to indicate a frequency at which the geographic locations have been previously-traveled.

2. The apparatus of claim 1, wherein the information associated with the user's boat includes dimensions of the user's boat.

3. The apparatus of claim 2, wherein the stored dimensions of the user's boat include a width and a depth below water of the user's boat.

4. The apparatus of claim 3, wherein the comparison locates stored routes traveled by other users having a boat with a width or a depth below water exceeding the width or the depth below water of the user's boat.

5. The apparatus of claim 2, wherein the stored dimensions of the user's boat include a height above water of the user's boat.

6. The apparatus of claim 1, wherein the comparison locates stored routes previously traveled by users having a boat with a width or a depth below water similar to the user's boat.

7. The apparatus of claim 1, wherein the processing device is further configured to receive tide related information from the user.

8. The apparatus of claim 1, wherein the processing device is further configured to identify geographic locations of points along the routes affected by tide based on a time of day or a time of year.

9. The apparatus of claim 8, wherein the processing device is further configured to visually indicate popularity of the stored routes based on tide related information.

10. The apparatus of claim 1, wherein the stored information associated with the boat used to travel the routes includes dimensions of the boat, the dimensions including a width of the boat and a depth below water of the boat.

11. The apparatus of claim 1, wherein the at least one of the stored routes suggested to the user based on the comparison is provided to the user as a course file.

12. The apparatus of claim 1, wherein the processing device is further configured to receive a desired geographic area from the user and wherein the processing device suggests a stored route in the desired geographic area.

13. The apparatus of claim 1, wherein the stored route data includes an identification of the users who traveled each of the routes, and wherein the processing device suggests a stored route previously traveled by a particular user.

14. An Internet-accessible computer system for providing route information to a user, the system comprising:

a non-transitory computer readable memory for receiving and storing dimensions of the user's boat and route data for a plurality of routes previously traveled by a plurality of users on a boat, the stored route data including geographic locations of points along the routes, information relating to the number of times or how frequently the users traveled the routes or passed through the geographic locations of points along the routes, and information associated with the boat used to travel the routes; and a processing device coupled with the memory and configured to display information about at least some of the stored routes previously traveled by users, receive information associated with the user's boat from the user, compare the information associated with the user's boat with the stored route data to locate stored routes previously traveled by users having a boat with a width or a depth below water similar to the user's boat, suggest at least one of the stored routes to the user based on the comparison, and visually indicate with a color-coded heat map a popularity of the suggested routes, the heat map associating a distinguishable color with geographic locations associated with the stored routes to indicate a frequency at which the geographic locations have been previously-traveled.

15. The computer system of claim 14, wherein the stored dimensions of the user's boat include a width and a depth below water of the user's boat.

16. The computer system of claim 15, wherein the stored information associated with the boat used to travel the routes includes dimensions of the boat, the dimensions including a width of the boat and a depth below water of the boat.

17. The computer system of claim 14, wherein the stored dimensions of the user's boat include a height above water of the user's boat.

18. The computer system of claim 14, wherein the comparison locates stored routes traveled by other users having a boat with a width or a depth below water exceeding the width or the depth below water of the user's boat.

19. The computer system of claim 14, wherein the processing device is further configured to receive tide related information from the user and identify geographic locations of points along the routes affected by tide based on a time of day or a time of year.

20. The computer system of claim 19, wherein the processing device is further configured to visually indicate popularity of the stored routes based on tide related information.

* * * * *